United States Patent [19]

Evans et al.

[11] 4,151,356
[45] Apr. 24, 1979

[54] 5-TRIAZIN-2-YL PHOSPHONATES

[75] Inventors: Samuel Evans, Basel; Michael Rasberger, Riehen, both of Switzerland

[73] Assignee: Ciba-Geigy Corporation, Ardsley, N.Y.

[21] Appl. No.: 840,705

[22] Filed: Oct. 11, 1977

[30] Foreign Application Priority Data

Oct. 18, 1976 [CH] Switzerland ............... 13165/76

[51] Int. Cl.$^2$ ........................... C07D 251/48
[52] U.S. Cl. ........................... 544/195; 544/214; 260/45.8 NT
[58] Field of Search ........................... 544/195, 214

[56] References Cited

U.S. PATENT DOCUMENTS

| | | | |
|---|---|---|---|
| 2,685,581 | 8/1954 | Coover | 544/214 |
| 3,158,450 | 11/1964 | D'Alelio | 544/214 |
| 3,165,513 | 1/1965 | D'Alelio | 544/214 |

*Primary Examiner*—John M. Ford
*Attorney, Agent, or Firm*—Wenderoth, Lind & Ponack

[57] ABSTRACT

A triazine of the formula I

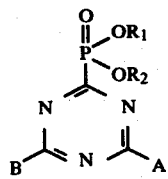

in which $R_1$ and $R_2$ independently of one another are hydrogen, $C_1$-$C_{18}$-alkyl, $C_6$-$C_{18}$-aryl, $C_7$-$C_{18}$-aralkyl or a radical of the formula II or III

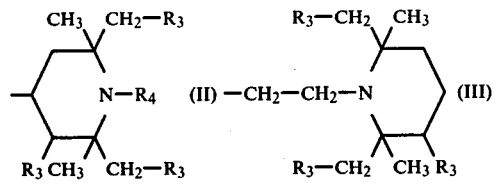

in which $R_3$ is hydrogen or $C_1$-$C_8$-alkyl and $R_4$ is hydrogen, oxyl, $C_1$-$C_{12}$-alkyl, $C_3$-$C_6$-alkenyl, $C_3$-$C_4$-alkinyl, $C_2$-$C_{21}$-alkoxyalkyl, $C_7$-$C_8$-aralkyl, 2,3-epoxypropyl, an aliphatic acyl group with 1-9 C atoms or one of the groups —$CH_2COOR_5$, —$CH_2$—$CH(R_6)$—$OR_7$, —$COOR_8$ or —$CONHR_8$, in which $R_5$ is $C_1$-$C_{12}$-alkyl, $C_3$-$C_6$-alkenyl, phenyl, $C_7$-$C_8$-aralkyl or cyclohexyl and $R_6$ is hydrogen, methyl or phenyl and $R_7$ denotes hydrogen, an aliphatic or aromatic, araliphatic or alicyclic acyl group with 1-18 C atoms, in which the aromatic part can optionally be substituted by chlorine, $C_1$-$C_4$-alkyl or $C_1$-$C_8$-alkoxy and/or by hydroxyl, and $R_8$ denotes $C_1$-$C_{12}$-alkyl, cyclohexyl, phenyl or benzyl and A is a radical of the formula IV or V

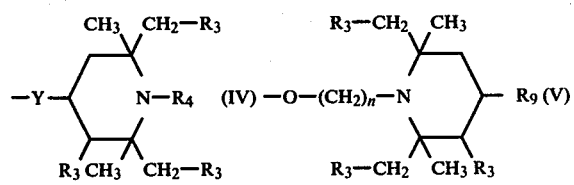

in which $R_3$ and $R_4$ have the above meaning, n is 1, 2 or 3 and $R_9$ is hydrogen or hydroxyl and Y is —O— or —$NR_{10}$—, in which $R_{10}$ is hydrogen, $C_1$-$C_{18}$-alkyl, $C_6$-$C_{10}$-aryl, $C_7$-$C_{18}$-aralkyl or a radical of the formula II with the above meaning, or A is —P(=O)(OR$_1$)OR$_2$, —S—$R_{11}$, —$NR_{12}R_{13}$ or —$OR_{14}$, in which $R_1$ and $R_2$ have the above meaning, $R_{11}$ is $C_1$-$C_{18}$-alkyl, $C_5$-$C_7$-cycloalkyl, $C_6$-$C_{10}$-aryl, $C_7$-$C_9$-aralkyl or the group —($C_pH_{2p}$)—CO—$OR_{15}$, in which $R_{15}$ is $C_1$-$C_{18}$-alkyl, and p denotes 1 to 6 and $R_{12}$ and $R_{13}$ independently of one another are hydrogen, $C_1$-$C_{18}$-alkyl, $C_3$-$C_4$-alkenyl, $C_5$-$C_7$-cycloalkyl, $C_6$-$C_{10}$-aryl, $C_7$-$C_9$-aralkyl or a radical of the formula II with the above meaning, and $R_{14}$ denotes $C_1$-$C_{18}$-alkyl, $C_6$-$C_{10}$-aryl or $C_7$-$C_9$-aralkyl, and B is a radical of the formula IV or V with the above meaning or is —P(=O)(OR$_1$)OR$_2$, in which $R_1$ is a radical of the formula II or III with the above meaning and $R_2$ has the above meaning, and its salts, as additives for stabilizing organic material.

5 Claims, No Drawings

5-TRIAZIN-2-YL PHOSPHONATES

The present invention relates to new s-triazin-2-ylphosphonates, their manufacture and their use for stabilising organic material and to the organic material protected, with the aid of these compounds, against oxidative and light-induced degradation.

s-Triazines which carry phenolic radicals and are suitable as antioxidants for organic polymers are known from U.S. Pat. No. 3,255,191. However, in some applications, phenolic stabilisers exhibit properties which restrict their use, such as discolorations in the substrate.

In industry there is, therefore, a need for phenol-free stabilisers for certain applications, especially for the protection of organic polymers against oxidative degradation. It is known from British Pat. No. 1,939,551 to use piperidine derivatives of s-triazine as light stabilisers, but these stabilisers do not have an antioxidative protective action or have such an action only to a minor extent.

A new category of s-triazin-2-ylphosphonates which, whilst they have excellent stabiliser properties, do not display these disadvantages, or do not display these disadvantages to only a considerably lesser extent, has now been found.

Accordingly, the invention relates to triazines of the formula I

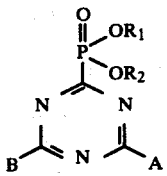

in which $R_1$ and $R_2$ independently of one another are hydrogen, $C_1$–$C_{18}$-alkyl, $C_6$–$C_{18}$-aryl, $C_7$–$C_{18}$-aralkyl or a radical of the formula II or III

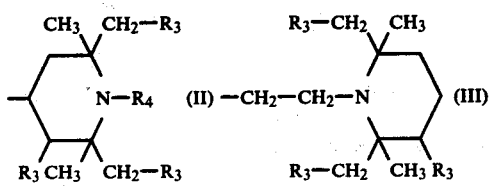

in which $R_3$ is hydrogen or $C_1$–$C_8$-alkyl and $R_4$ is hydrogen, oxyl, $C_1$–$C_{12}$-alkyl, $C_3$–$C_6$-alkenyl, $C_3$–$C_4$-alkinyl, $C_2$–$C_{21}$-alkoxyalkyl, $C_7$–$C_8$-aralkyl, 2,3-epoxypropyl, an aliphatic acyl group with 1–9 C atoms or one of the groups —$CH_2COOR_5$, —$CH_2$—$CH(R_6)$—$OR_7$, —$COOR_8$ or —$CONHR_8$, in which $R_5$ is $C_1$–$C_{12}$-alkyl, $C_3$–$C_6$-alkenyl, phenyl, $C_7$–$C_8$-aralkyl or cyclohexyl and $R_6$ is hydrogen, methyl or phenyl and $R_7$ denotes hydrogen, an aliphatic or aromatic, araliphatic or alicyclic acyl group with 1–18 C atoms, in which the aromatic part can optionally be substituted by chlorine, $C_1$–$C_4$-alkyl or $C_1$–$C_8$-alkoxy and/or by hydroxyl, and $R_8$ denotes $C_1$–$C_{12}$-alkyl, cyclohexyl, phenyl or benzyl and A is a radical of the formula IV or V

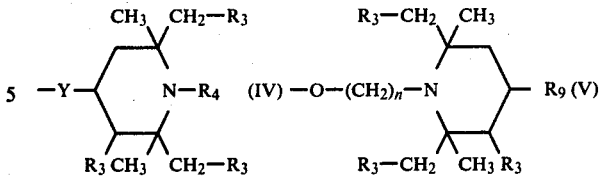

in which $R_3$ and $R_4$ have the above meaning, n is 1, 2 or 3 and $R_9$ is hydrogen or hydroxyl and Y is —O— or —$NR_{10}$—, in which $R_{10}$ is hydrogen, $C_1$–$C_{18}$-alkyl, $C_6$–$C_{10}$-aryl, $C_7$–$C_{18}$-aralkyl or a radical of the formula II with the above meaning, or A is —$P(=O)(OR_1)OR_2$, —$S$—$R_{11}$, —$NR_{12}R_{13}$ or —$OR_{14}$, in which $R_1$ and $R_2$ have the above meaning, $R_{11}$ is $C_1$–$C_{18}$-alkyl, $C_5$–$C_7$-cycloalkyl, $C_6$–$C_{10}$-aryl, $C_7$–$C_9$-aralkyl or the group —$(C_pH_{2p})$—$CO$—$OR_{15}$, in which $R_{15}$ is $C_1$–$C_{18}$-alkyl, and p denotes 1 to 6 and $R_{12}$ and $R_{13}$ independently of one another are hydrogen, $C_1$–$C_{18}$-alkyl, $C_3$–$C_6$-alkenyl, $C_5$–$C_7$-cycloalkyl, $C_6$–$C_{10}$-aryl, $C_7$–$C_9$-aralkyl or a radical of the formula II with the above meaning, and $R_{14}$ denotes $C_1$–$C_{18}$-alkyl, $C_6$–$C_{10}$-aryl or $C_7$–$C_9$-aralkyl, and B is a radical of the formula IV or V with the above meaning or is —$P(=O)(OR_1)OR_2$, in which $R_1$ is a radical of the formula II or III with the above meaning and $R_2$ has the above meaning, and their salts.

As $C_1$–$C_{18}$-alkyl, $R_1$ and $R_2$ denote branched or, in particular, unbranched $C_1$–$C_{18}$-alkyl, above all $C_1$–$C_{12}$-alkyl, such as methyl, ethyl, isopropyl, sec.-butyl, tert.-butyl, amyl, n-hexyl, 1,1,3,3-tetramethylbutyl, tert.-nonyl, n-decyl or n-dodecyl. As alkyl groups, $R_1$ and $R_2$ are preferably alkyl groups with 1–3 C atoms and in particular methyl or ethyl.

As $C_6$–$C_{18}$-aryl, $R_1$ and $R_2$ denote substituted or, in particularly, unsubstituted aryl, such as naphthyl or, above all, phenyl.

As $C_7$–$C_{18}$-aralkyl, $R_1$ and $R_2$ denote substituted or, in particular, unsubstituted aralkyl with, in particular, 1–3 C atoms in the alkyl part, such as benzyl, α-phenylethyl or 2-phenylpropyl, especially benzyl.

As $C_1$–$C_8$-alkyl, $R_3$ is, for example, methyl, ethyl, iso-propyl, n-butyl, amyl, n-hexyl or n-octyl. Alkyl groups with 1–4 C atoms and especially ethyl and methyl are preferred. Compounds in which $R_3$ denotes methyl are to be singled out in particular.

As $C_1$–$C_{12}$-alkyl, $R_4$ is, for example, methyl, ethyl, n-propyl, n-butyl, n-pentyl, n-hexyl, n-octyl, n-decyl or n-dodecyl. Alkyl groups with 1–8 C atoms, especially those with 1–4 atoms, and above all methyl are preferred.

As $C_3$–$C_6$-alkenyl, $R_4$ is, for example, allyl, 2-butenyl or 2-hexenyl, especially allyl.

As $C_3$–$C_4$-alkinyl, $R_4$ is, for example, propargyl.

If $R_4$ denotes $C_2$–$C_{21}$-alkoxyalkyl, the alkyl part can contain 1–3 C atoms and the alkoxy part can consist of 1–18 C atoms, such as in, for example, methoxymethyl, ethoxymethyl, 2-methoxyethyl, 2-ethoxyethyl, 2-n-butoxyethyl, 3-n-butoxyethyl, 2-octoxyethyl or 2-octadecyloxyethyl. Compounds in which $R_4$ denotes an alkoxy group with 2–6 C atoms are to be mentioned in particular.

As $C_7$–$C_9$-aralkyl, $R_4$ is, for example, benzyl α-phenylethyl or α,α-dimethylbenzyl.

As an aliphatic acyl group with 1–9 atoms, $R_4$ is, for example, formyl, acetyl, acryloyl or crotonyl.

If $R_4$ is the group —$CH_2COOR_5$, $R_5$, as $C_1$–$C_{12}$-alkyl, denotes, for example, methyl, ethyl, isopropyl, n-butyl, iso-butyl, t-butyl, isopentyl, n-octyl, n-decyl or n-dodecyl. $R_5$ is preferably $C_1$–$C_4$-alkyl. As $C_3$–$C_6$-alkenyl, $R_5$ is, for example, allyl, 2-butenyl or 2-hexenyl. As $C_7$–$C_8$-aralkyl, $R_5$ is, for example, benzyl or α-phenylethyl.

If $R_4$ is the group —$CH_2$—$CH(R_6)$—$OR_7$, $R_6$ denotes hydrogen, methyl or phenyl, especially hydrogen. As an aliphatic, aromatic, alicyclic or araliphatic $C_1$–$C_{18}$-aryl radical which is optionally substituted in the aromatic part by chlorine or $C_1$–$C_4$-alkyl, such as methyl, ethyl, n-propyl or t-butyl, or by $C_1$–$C_8$-alkoxy, such as methoxy, ethoxy, butoxy or octoxy, and/or by hydroxyl, $R_7$ is, for example, acetyl, propionyl, butyroyl, octanoyl, dodecanoyl, stearoyl, acryloyl, benzoyl, chlorobenzoyl, toluoyl, isopropylbenzoyl, 2,4-dichlorobenzoyl, 4-methoxybenzoyl, 3-butoxybenzoyl, 2-hydroxybenzoyl, 3,5-di-t-butyl-4-hydroxybenzoyl, β-(3,5-di-t-butyl-4-hydroxyphenyl)-propionyl, phenylacetyl, cinnamoyl or hexahydrobenzoyl.

If $R_4$ is the group —$COOR_8$, $R_8$, as $C_1$–$C_{12}$-alkyl, is, for example, methyl, ethyl, isobutyl, n-hexyl, n-octyl, n-decyl or n-dodecyl. Alkyl groups with 1–4 C atoms are preferred as $R_8$. The same applies when $R_4$ is —$CONHR_8$.

If $R_5$ and $R_8$ are $C_1$–$C_{12}$-alkyl, the meanings are, in particular, those indicated for $R_1$.

If $R_5$, $R_{12}$ and $R_{13}$ are $C_3$–$C_6$-alkenyl, the meanings are, in particular, those indicated for $R_4$.

If $R_5$ is $C_7$–$C_8$-aralkyl, the latter is, in particular, α-phenylethyl and above all, benzyl.

n is preferably 2.

If $R_{10}$ is $C_1$–$C_{18}$-alkyl, the meanings are, in particular, those indicated for $R_1$. If $R_{10}$ is $C_6$–$C_{10}$-aryl, the latter is, in particular, naphthyl and above all phenyl. If $R_{10}$ is $C_7$–$C_{18}$-aralkyl, the meanings are, in particular, those indicated for $R_1$.

As $C_1$–$C_{18}$-alkyl, $R_{11}$, $R_{15}$, $R_{12}$ and $R_{13}$ are, for example, methyl, ethyl, isopropyl, n-butyl, n-pentyl, n-hexyl, n-octyl, n-decyl, n-dodecyl, n-tetradecyl, n-hexadecyl or n-octadecyl; $R_{11}$ and $R_{13}$ are preferably an alkyl group with 1–12 C atoms and especially an alkyl group with 8 C atoms.

As $C_5$–$C_7$-cycloalkyl, $R_{11}$, $R_{12}$ and $R_{13}$ are, for example, cyclopentyl, methylcyclopentyl, cyclohexyl or methylcyclohexyl, preferably cyclohexyl.

As $C_6$–$C_{10}$-aryl, $R_{11}$, $R_{12}$ and $R_{13}$ are, for example, phenyl, α-naphthyl or β-naphthyl, especially phenyl.

As $C_7$–$C_9$-aralkyl, $R_{11}$, $R_{12}$ and $R_{13}$ are, for example, benzyl, α-ethylphenyl or α,α-dimethylbenzyl.

As $C_1$–$C_{18}$-alkyl, $R_{14}$ is, for example, methyl, ethyl, isopropyl, n-butyl, sec.-butyl, t-butyl, amyl, n-hexyl, n-octyl, n-decyl, n-dodecyl, n-tetradecyl, n-hexadecyl or n-octadecyl. Preferably, $R_{14}$ is an alkyl group with 1–12, and especially with 1–4, C atoms. Particularly preferentially, $R_{14}$ is ethyl, propyl or butyl.

As $C_6$–$C_{10}$-aryl, $R_4$ is, for example, phenyl, α-naphthyl or β-naphtyl, especially phenyl.

As $C_7$–$C_9$-aralkyl, $R_{14}$ is, for example, benzyl, α-ethylphenyl or α,α-dimethylbenzyl.

Salts which may be mentioned of compounds of the formula I are, in particular, addition salts with inorganic or organic acids or bases. The salts can be obtained in the customary manner and the free bases, which, in turn, are preferred, can be re-isolated from the salts. Suitable acids for salt formation are, in particular, inorganic acids, such as hydrochloric acid, sulphuric acid and phosphoric acid, but also acids, such as, for example, p-toluene-sulphonic acid. Suitable bases are organic and, in particular, inorganic bases, such as oxides or hydroxides of metals, such as alkali metals or alkaline earth metals, for example sodium, barium, zinc, cobalt or nickel.

Triazines of the formula I in which $R_1$ is $C_1$–$C_{12}$-alkyl, naphthyl, phenyl, $C_7$–$C_9$-aralkyl or a radical of the formula II or III, $R_2$ is $C_1$–$C_{12}$-alkyl, naphthyl, phenyl or $C_7$–$C_9$-aralkyl, $R_3$ is hydrogen or $C_1$–$C_4$-alkyl and $R_4$ is hydrogen, oxyl, $C_1$–$C_8$-alkyl, $C_3$–$C_4$-alkenyl or alkinyl, $C_2$–$C_6$-alkoxyalkyl, $C_7$–$C_9$-aralkyl, acetyl, acryloyl or crotonoyl, or one of the groups —$CH_2$—$COOR_5$, —$CH_2$—$CH(R_6)$—$OR_7$, —$COOR_8$ or —$CONHR_8$, in which $R_5$ is $C_1$–$C_4$-alkyl, $C_3$–$C_4$-alkenyl, phenyl, $C_7$–$C_8$-aralkyl or cyclohexyl and $R_6$ is hydrogen, methyl or phenyl and $R_7$ denotes hydrogen or an aliphatic, aromatic, alicyclic or araliphatic acyl group with 1–18 C atoms, in which the aromatic part can optionally be substituted by chlorine, $C_1$–$C_4$-alkyl or $C_1$–$C_8$-alkoxy and/or hydroxyl, and $R_8$ is $C_1$–$C_{12}$-alkyl, and A is a radical of the formula IV or V, in which $R_3$ and $R_4$ have the above meaning, n is 2, $R_9$ is hydrogen or hydroxyl, Y is —O— or —$NR_{10}$—, in which $R_{10}$ is hydrogen, straight-chain $C_1$–$C_8$-alkyl or a radical of the formula II with the above meaning, or A is —$P(=O)(OR_1)OR_2$, —S—$R_{11}$, —$NR_{12}R_{13}$ or —$OR_{14}$, in which $R_1$ and $R_2$ have the above meaning, $R_{11}$ denotes $C_1$–$C_{18}$-alkyl or the group —$(C_pH_{2-p})$—CO—$OR_{15}$, in which $R_{15}$ denotes $C_1$–$C_{18}$-alkyl and p is 1 to 4, and $R_{14}$ is $C_1$–$C_{12}$-alkyl and $R_{12}$ and $R_{13}$ independently of one another are hydrogen, $C_1$–$C_{12}$-alkyl, phenyl or a radical of the formula II with the above meaning and B is a radical of the formula IV or V with the above meaning or is —$P(=O)(OR_1)OR_2$ in which $R_1$ is a radical of the formula II or III with the above meaning, and $R_2$ has the above meaning, are preferred.

Triazines of the formula I in which $R_1$ is $C_1$–$C_3$-alkyl or a radical of the formula II, $R_2$ is $C_1$–$C_3$-alkyl, $R_3$ denotes hydrogen, methyl or ethyl and $R_4$ is hydrogen, $C_1$–$C_4$-alkyl, allyl, propargyl, $C_2$–$C_6$-alkoxyalkyl, acetyl, acryloyl or crotonoyl, or one of the groups —$CH_2$—$COOR_5$, —$CH_2$—$CH(R_6)$—$OR_7$, —$COOR_8$ or —$CONHR_8$, in which $R_5$ is $C_1$–$C_4$-alkyl and $R_6$ denotes hydrogen or methyl and $R_7$ denotes hydrogen and $R_8$ is $C_1$–$C_4$-alkyl, and A is a radical of the formula IV or V, in which $R_3$ and $R_4$ have the above meaning and n is 2 and $R_9$ is hydrogen or hydroxyl, Y is —$NR_{10}$—, in which $R_{10}$ is hydrogen or a radical of the formula II with the above meaning, or A is —$P(=O)(OR_1)OR_2$, in which $R_1$ and $R_2$ have the above meaning, and B is a radical of the formula IV or V, in which $R_3$ and $R_4$ have the above meaning, n is 2 and $R_9$ is hydrogen or hydroxyl, or B is —$P(=O)(OR_1)OR_2$, in which $R_1$ is a radical of the formula II with the above meaning and $R_2$ has the above meaning, are particularly preferred.

Triazines of the formula I in which $R_1$ is $C_1$–$C_3$-alkyl or a radical of the formula II, $R_2$ is $C_1$–$C_3$-alkyl, $R_3$ denotes hydrogen or methyl and $R_4$ denotes hydrogen or methyl and A is a radical of the formula IV or V, in which $R_3$ and $R_4$ have the above meaning, n is 2 and $R_9$ is hydrogen or hydroxyl, Y is —$NR_{10}$—, in which $R_{10}$ is hydrogen or a radical of the formula II with the above meaning, or A is —$P(=O)(OR_1)OR_2$, in which $R_1$ and $R_2$ have the above meaning, and B is a radical of the formula IV or V, in which $R_3$, $R_4$ and n have the above meaning, and $R_9$ is hydrogen or hydroxyl, or B is —$P(=O)(OR_1)OR_2$, in which $R_1$ is a radical of the formula II with the above meaning and $R_2$ has the above meaning, are very particularly preferred.

The compounds which are mentioned in the examples should be singled out above all.

The triazines according to the invention can be manufactured by methods which are in themselves known.

In general, the starting material used is 2,4,6-trichloro-1,3,5-triazine, which is a known compound. A —P(=O)(OR$_1$)(OR$_2$) radical is first introduced into this and a —B radical is then introduced, or the procedure is reversed. A —P(=O)(OR$_1$)OR$_2$ radical can be introduced in a manner which is in itself known, say by means of the known Arbusov reaction, in which 2,4,6-trichloro-1,3,5-triazine is reacted with a phosphite of the formula P(OR$_1$)(OR$_2$)$_2$ in the presence of a salt, such as NiCl$_2$·6H$_2$O. The phosphite can at the same time serve as the solvent. If a —B radical is a radical of the formula —P(=O)(OR$_1$)OR$_2$, it is introduced in the same way, optionally at the same time as the first-mentioned substitution. If a —B radical is a radical of the formulae IV or V, a 4,6-dichloro-1,3,5-triazine phosphonate, obtained as above, is reacted with the alcohol which corresponds to the formula IV or V or with the amine which corresponds to the formula IV, or, alternatively, 2,4,6-trichloro-1,3,5-triazine is reacted with the alcohol which corresponds to the formula IV or V or with the amine which corresponds to the formula IV and the reaction product is subsequently phosphorylated as described above.

The triazines, according to the invention, of the formula I are then obtained by introducing the radical A into a chloro-triazine of the formula VI

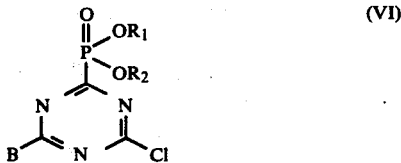

(VI)

The radical A can be introduced by methods which are in themselves known. If A is a radical of the formula IV or V, it is possible, for example, to react a chloro-triazine of the formula VI with the alcohol which corresponds to the formula IV or V or with the amine which corresponds to the formula IV, preferably in the presence of a base and/or of a solvent.

Examples of suitable bases are organic nitrogen bases, such as triethylamine, pyridine or piperidine. Inorganic bases, such as alkali metal carbonates or alkali metal hydroxides, preferably sodium carbonate, are also suitable. Suitable solvents are all adequately polar protic and aprotic solvents, such as, for example, acetone, acetone/water, methanol, ethanol, tetrahydrofurane or diethyl ether. Acetone, acetone/water, methanol or ethanol are preferably used. If A is a —P(=O)(OR$_1$)OR$_2$ radical, the latter can be introduced, in particular, in the manner described above, for example by reacting a chloro-triazine of the formula VI with a phosphite of the formula P(OR$_1$)(OR$_2$)$_2$. If A is a —S—R$_{11}$, —NR$_{12}$R$_{13}$ or —O—R$_{14}$ radical, the latter is introduced, in particular in the manner described in British Patent No. 1,393,551. For this reaction, an alkali metal mercaptide, an alkali metal phenolate or an amine of the formulae MS—R$_{11}$, MO—R$_{14}$ or HNR$_{12}$R$_{13}$ is preferably reacted in a solvent. The amine of the formula HNR$_{12}$R$_{13}$ is preferably employed in excess.

Replacement of the third chlorine atom in the compound of the formula VI is frequently not easy to carry out and depends greatly on the nucleophilic character of the attacking group. The best results are achieved when this reaction stage is carried out at elevated temperature, preferably at the reflux temperature.

The piperidine-alcohols which correspond to the formulae IV and V and the piperidine-amines which correspond to the formula IV are known, for example 4-hydroxy-piperidines are known from German Offenlegungsschrift No. 2,352,658 and 4-amino-piperidines are known from U.S. Pat. No. 3,684,765. The 4-OH compounds can generally be manufactured from the corresponding 4-oxo-piperidines by reduction, for example catalytic hydrogenation over Raney nickel, whilst the 4-NH$_2$ compounds are obtainable from a 4-oxo compound, for example by means of reductive reaction with ammonia.

The 4-oxo-piperidines, in turn, can be manufactured by various processes.

Thus, for example, the reaction of an aliphatic ketone with ammonia is described by W. Traube in Chem. Ber. 41, 777 (1908).

4-Oxo-piperidines which are unsubstituted on the nitrogen atom can also be manufactured analogously to the process described in U.S. Pat. No. 3,513,170. In this reaction, a tetrahydropyrimidine which is substituted by alkyl is rearranged by hydrolysis in the presence of an acid catalyst.

4-Oxo-N—H compounds which possess substituents of different types in the 2-position and the 6-position can be manufactured by reacting a ketone of the formula CH$_3$—CO—CH$_2$—R$_3$ with ammonia. The pyrimidine formed is hydrolysed as described in Helv. Chim. Acta 30, 114 (1947) to give an aminoketone. This is reacted, in a second process step, with ammonia and a ketone CH$_3$—CO—CH$_2$—R$_3$, as is described, for example, in Monatsh. Chemie 88, 464 (1957). N—H compounds can be obtained from the pyrimidine, which results from this reaction, by hydrolysis.

Derivatives can be manufactured from the corresponding N—H compounds by substitution on the N atom. The reactions concerned are the substitution reactions customary for secondary amines although, because of the steric hindrance due to the methyl group or the group —CH$_2$—R$_3$, these proceed more slowly. The N—H compounds can, for example, be reacted with alkyl halides, alkenyl halides, aralkyl halides or alkoxyalkyl halides, with dialkyl sulphates, with epichlorohydrin, with esters of chloro-carboxylic acids, such as chloroacetates, or acid chlorides or acid anhydrides.

The group —CH$_2$—CH(R$_6$)—OR$_7$ can be introduced by reacting the N—H-piperidines with an epoxide of the formula

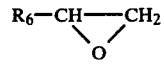

and subsequently acylating the reaction product with an acyl chloride of the formula R$_7$Cl.

In principle, the amines which contain the radical HNR$_{10}$— bonded to a radical of the formula IV are manufactured in an analogous manner. The introduction of the group R$_{10}$ is described, for example, in German Offenlegungsschrift No. 2,349,962 and is effected by reacting the corresponding amine with a chloride R$_{10}$Cl, especially in the presence of an acid-binding agent. However, it is also possible to react a corresponding 4-oxo-piperidine with a corresponding 4-aminopiperidine, especially with catalytic hydrogenation, such as with Raney nickel and hydrogen. (Bis-2,2,6,6-tetramethylpiperidin-4-yl)-amine, for example, is obtained in this way.

Piperidines which can be used as starting materials for the introduction of the radicals of the formula IV or V are, for example, those which follow: 2,2,6,6-tetramethyl-4-hydroxy-piperidine, 2,2,6,6-tetramethyl-4-amino-piperidine, 2,3,6-trimethyl-2,6-diethyl-4-hydroxy-piperidine, N-acetyl-2,2,6,6-tetramethyl-4-hydroxy-piperidine, N-methyl-2,2,6,6-tetramethyl-4-amino-piperidine, 1-(2-hydroxyethyl)-2,2,6,6-tetramethyl-4-hydroxy-piperidine, 1-(2-hydroxyethyl)-2,2,6,6-tetramethylpiperidine and (bis-2,2,6,6-tetramethylpiperidin-4-yl)-amine.

The following mercaptans can, for example, be used as starting materials: propyl-mercaptan, 2-butyl-mercaptan, octyl-mercaptan, decyl-mercaptan, dodecyl-mercaptan and octadecyl-mercaptan; methyl mercapto-acetate, ethyl mercaptoacetate, propyl mercaptoacetate and dodecyl mercaptoacetate (thioglycollates); and methyl 3-mercapto-propionate, ethyl 3-mercapto-propionate, propyl 3-mercapto-propionate and dodecyl 3-mercapto-propionate (3-mercaptopropionates).

The following phosphites can, for example, be used as starting materials: trimethyl phosphite, triethyl phosphite, triisopropyl phosphite, tridecyl phosphite, tridodecyl phosphite, diethyl 2,2,6,6-tetramethylpiperidin-4-yl phosphite, di-n-propyl 1,2,2,6,6-pentamethylpiperidin-4-yl phosphite and dimethyl 2,3,6-trimethyl-2,6-diethylpiperidin-4-yl phosphite.

The following amines or alcohols can, for example, be used as starting materials: phenylamine, benzylamine, ethylamine, cyclohexylamine and octylamine or phenyl alcohol, benzyl alcohol, ethyl alcohol, cyclohexyl alcohol and octyl alcohol.

According to the present invention, the compounds of the formula I can be used as stabilisers for plastics, to protect them against damage due to the action of oxygen, heat and light. Examples of such plastics are the polymers listed on pages 12-14 of German Offenlegungsschrift No. 2,456,864.

The stabilisation of polyolefins, styrene polymers and polyurethanes and of polyamides is of particular importance and the compounds of the formula I are outstandingly suitable for this. Examples of such polymers are high density polyethylene and low density polyethylene, polypropylene, ethylene/propylene copolymers, polystyrene, styrene/butadiene/acrylonitrile copolymers, mixtures of polyolefins or of styrene polymers, polyamides and polyurethanes, in the form of films, fibres, lacquers, elastomers or foams.

The stabilisers are added to the plastics in a concentration of 0.01 to 5% by weight, calculated relative to the material to be stabilised. Preferably, 0.03 to 1.5, and particularly preferentially 0.2 to 0.6, % by weight of the compounds, calculated relative to the material to be stabilised, are incorporated into the latter.

Incorporation can be effected after polymerisation, for example by mixing the compounds, and optionally further additives, into the melt by the methods customary in the art, before or during shaping, or by applying the dissolved or dispersed compounds to the polymer, if necessary with subsequent evaporation of the solvent.

The new compounds can also be added to the plastics to be stabilised in the form of a master batch which contains these compounds, for example in a concentration of 2.5 to 25% by weight.

In the case of crosslinked polyethylene, the compounds are added prior to crosslinking.

The invention therefore also relates to plastics stabilised by the addition of 0.01 to 5% by weight of a compound of the formula I, which plastics optionally can contain yet further known and customary additives. The plastics stabilised in this way can be used in very diverse forms, for example as films, fibres, tapes or profiles, or as binders for lacquers, adhesives or putties.

Examples which may be mentioned of further additives, together with which the stabilisers which can be used according to the invention can be employed, are those which follow: antioxidants, such as simple 2,6-dialkylphenols, derivatives of alkylated hydroquinones, hydroxylated thiodiphenyl ethers, alkylidene-bis-phenols, O—, N— and S-benzyl compounds, hydroxybenzylated malonates, hydroxybenzyl-aromatic compounds, s-triazine compounds, amides of $\beta$-(3,5-di-tert.-butyl-4-hydroxyphenyl)-propionic acid, esters of $\beta$-(3,5-di-tert.-butyl-4-hydroxyphenyl)-propionic acid, esters of $\beta$-(5-tert.-butyl-4-hydroxy-3-methylphenyl)-propionic acid, esters of 3,5-di-tert.-butyl-4-hydroxyphenylacetic acid, acylaminophenols, benzylphosphonates and aminoaryl derivatives, UV absorbers and light stabilisers such as 2-(2'-hydroxyphenyl)-benztriazoles, 2,4-bis-(2'-hydroxyphenyl)-6-alkyl-s-triazines, 2-hydroxybenzophenones, 1,3-bis-(2'-hydroxybenzoyl)-benzenes, esters of optionally substituted benzoic acids and acrylates and, furthermore, nickel compounds, sterically hindered amines, oxalic acid diamides, metal deactivators, phosphites, compounds which destroy peroxide, polyamide stabilisers, basic costabilisers, PVC stabilisers, nucleating agents or other additives, such as, for example, plasticisers, lubricants, emulsifiers, fillers, carbon black, asbestos, kaolin, talc, glass fibres, pigments, optical brighteners, flameproofing agents and antistatic agents.

Examples of further additives, together with which the stabilisers which can be used according to the invention can be employed, are given on pages 18 to 24 in German Offenlegungsschrift No. 2,427,853.

The manufacture and use of the compounds according to the invention is described in more detail in the examples which follow.

EXAMPLE 1

2-(Diethylphosphono)-4,6-bis-[(2,2,6,6-tetramethylpiperidin-4-yl)-amino]-1,3,5-triazine (Stabiliser 1)

(a)

2-Chloro-4,6-bis-[(2,2,6,6-tetramethylpiperidin-4-yl)-amino]-1,3,5-triazine 62.4 g of 2,2,6,6-tetramethyl-4-amino-piperidine in 200 ml of acetone and, at the same time, 42.4 g of sodium carbonate dissolved in 100 ml of water are added to a finely dispersed suspension of cyanuric chloride, prepared by adding 36.9 g of the latter in 200 ml of boiling acetone to 400 ml of ice water. The temperature is kept at 0°–5° C. by means of external cooling. After the addition is complete, the reaction mixture is allowed slowly to warm to room temperature and is stirred at this temperature for 3 hours. Filtering and recrystallisation of the product from ethyl acetate/hexane gives 46.3 g of a white crystalline product, melting point 270° C.

(b)
2-(Diethylphosphono)-4,6-bis-[(2,2,6,6-tetramethyl-piperidin-4-yl)-amino]-1,3,5-triazine 41 g of the product obtained from (a) in 200 ml of triethyl phosphite are heated with 500 mg of $NiCl_2.2-H_2O$ (catalyst) to 180° C. for 10 hours in an autoclave. The reaction mixture is cooled to room temperature. The excess triethyl phosphite, which serves as a reactant and as the solvent, is evaporated under 12 mm Hg. The resulting solid product is washed several times with n-hexane in order to remove traces of triethyl phosphite and is then twice recrystallised from ethyl acetate/hexane to give 11.3 g of a white solid, melting point 195° C.

EXAMPLES 2 TO 15

The compounds which follow can be prepared in a manner analogous to that described in Example 1:
2. 2-(Diethylphosphono)-4,6-bis-[(2,2,6,6-tetramethyl-piperidin-4-yl)-amino]-1,3,5-triazine.
3. 2-[Ethyl-(2,2,6,6-tetramethylpiperidin-4-yl)-phosphono]-4,6-bis-[(2,2,6,6-tetramethyl-piperidin-4-yl)-amino]-1,3,5-triazine.
4. 2,4-Bis-(diethylphosphono)-6-[(2,2,6,6-tetramethyl-pipidin-4-yl)-amino]-1,3,5-triazine.
5. 2,4-Bis-(diisopropylphosphono)-6-[(1,2,2,6,6-pentamethyl-piperidin-4-yl)-oxy]-1,3,5-triazine.
6. 2-[Methyl-(2,3,6-trimethyl-2,6-diethyl-piperidin-4-yl)-phosphono]-4,6-bis-[2-(2,2,6,6-tetramethyl-piperidin-1-yl)-ethoxy]-1,3,5-triazine.
7. 2-(Diethylphosphono)-4-(2,2,6,6-tetramethyl-piperidin-1-yl)-6-n-octylmercapto-1,3,5-triazine.
8. 2,4,6-Tris-[ethyl-(1,2,2,6,6-pentamethyl-piperidin-4-yl)-phosphono]-1,3,5-triazine.
9. 2-(Diethylphosphono)-4-[(N-acetyl-2,2,6,6-tetramethyl-4-yl)-oxy]-6-(benzylamino)-1,3,5-triazine.
10. 2-(Di-n-octylphosphono)-4-[ethyl-(2,2,6,6-tetramethyl-piperidin-4-yl)-phosphono]-6-[(1,2,2,6,6-pentamethylpiperidin-4-yl)-amino]-1,3,5-triazine.
11. 2,4-Bis-[ethyl-(2,2,6,6-tetramethylpiperidin-4-yl)-phosphono]-6-[(1,2,2,6,6-pentamethyl-piperidin-4-yl)-oxy]-1,3,5-triazine.
12. 2-(Diethylphosphono)-4-[(2,2,6,6-tetramethylpiperidin-4-yl)-amino]-6-(n-octyl-thio)-1,3,5-triazine.
13. 2-[i-Propyl-(1,2,2,6,6-pentamethyl-piperidin-4-yl)-phosphono]-4-[(2,3,6-trimethyl-2,6-diethyl-piperidin-4-yl)-amino]-6-(ethoxycarbonylmethyl-thio)-1,3,5-triazine.
14. 2-(Di-isopropylphosphono)-4-[(1,2,2,6,6-pentamethyl-piperidin-4-yl)-amino]-6-(n-hexyloxy)-1,3,5-triazine.
15. 2-(Di-n-pentylphosphono)-4-[bis-(2,2,6,6-tetramethyl-piperidin-4-yl)-amino]-6-[(1,2,2,6,6-pentamethyl-piperidin-4-yl)-amino]-1,3,5-triazine.

EXAMPLE 16

100 parts of polypropylene (melt index 2.6 g/10 minutes, 230° C./2,160 g) are mixed intensively for 10 minutes, in a shaking apparatus, with 0.2 part of one of the additives listed in Table I which follows.

The resulting mixture is kneaded for 10 minutes at 200° in a Brabender plastograph and the composition obtained in this way is then pressed in a platen press at a plate temperature of 260° to give 1 mm thick sheets, from which strips 1 cm broad and 17 cm in length are punched.

The test to determine the effectiveness of the additives added to the test strips is carried out by heat-ageing in a circulating air oven at 135° and 149° and an additive-free test strip serves for comparison. 3 test strips from each formulation are employed for this test. The end point is defined as the start of decomposition of the test strip, which is easily recognisable from the complete embrittlement. The results are given in days.

Table I

| Stabiliser No. | Days to the start of decomposition | |
|---|---|---|
| | 135° C. | 149° C. |
| without an additive | 1 | <1 |
| 1 | 27 | 6 |

EXAMPLE 17

100 parts of polypropylene (melt index 2.6 g/10 minutes, 230° C./2,160 g) are mixed intensively for 10 minutes, in a shaking apparatus, with 0.1 part of one of the additives listed in Table II which follows and 0.3 part of dilauryl thiodipropionate: in other respects the procedure is as in Example 16. A test strip which contains only 0.3 part of dilauryl thiodipropionate serves for comparison.

Table II

| Stabiliser No. | Days to the start of decomposition | |
|---|---|---|
| | 135° C. | 149° C. |
| without an additive | 16 | 2 |
| 1 | 42 | 10 |

What is claimed is:
1. A member selected from the group consisting of a compound of the formula

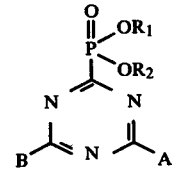

and a salt thereof,
wherein $R_1$ and $R_2$ independently represent hydrogen, $C_1-C_{18}$-alkyl, $C_6-C_{18}$-aryl, $C_7-C_{18}$-aralkyl or a radical of the formula II or III

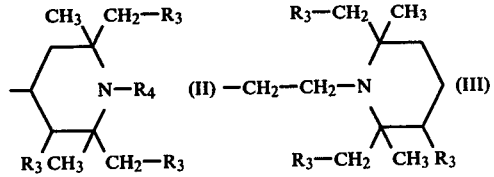

wherein $R_3$ is hydrogen or $C_1-C_8$-alkyl and $R_4$ is (1) hydrogen, (2) oxyl, (3) $C_1-C_{12}$-alkyl, (4) $C_3-C_6$-alkenyl, (5) $C_3-C_4$-alkinyl, (6) $C_2-C_{21}$-alkoxyalkyl, (7) $C_7-C_8$-aralkyl, (8) 2,3-epoxypropyl, (9) an aliphatic acyl group with 1–9 C atoms, (10) —$CH_2COOR_5$, (11) —$CH_2$—$CH(R_6)$—$OR_7$, (12) —$COOR_8$ or (13) —$CONHR_8$, wherein $R_5$ is (1) $C_1-C_{12}$-alkyl, (2) $C_3-C_6$-alkenyl, (3) phenyl, (4) $C_7-C_8$-aralkyl or (5) cyclohexyl and $R_6$ is hydrogen, methyl or phenyl and $R_7$ represents (1) hydrogen, (2) an aliphatic-, aromatic-, araliphatic- alicyclic acyl group having 1–18 C atoms, in which the aromatic acyl portion is unsubstituted or substitituted by at least one member of the group of chlorine, $C_1-C_4$-alkyl or $C_1-C_8$-alkoxy and by hydroxyl, and $R_8$ represents $C_1$-$C_{12}$-alkyl, cyclohexyl, phenyl or benzyl; A represents (1) a radical of the formula IV or V

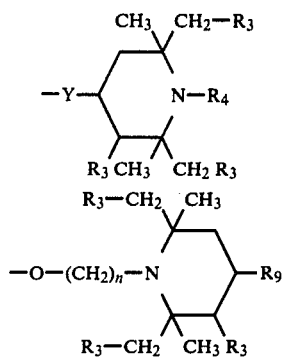

wherein $R_3$ and $R_4$ are as defined above, n is 1, 2 or 3 and $R_9$ is hydrogen or hydroxyl and Y is —O— or —$NR_{10}$—, wherein $R_{10}$ is (a) hydrogen, (b) $C_1$-$C_{18}$-alkyl, (c) $C_6$-$C_{10}$-aryl, (d) $C_7$-$C_{18}$-aralkyl or (e) a radical of the formula II as defined above, or (2) A is —P(=O)(OR$_1$)OR$_2$, —S—$R_{11}$, —$NR_{12}R_{13}$ or —$OR_{14}$, wherein $R_1$ and $R_2$ are as defined above, $R_{11}$ is (1) $C_1$-$C_{18}$-alkyl, (2) $C_5$-$C_7$-cycloalkyl, (3) $C_6$-$C_{10}$-aryl, (4) $C_7$-$C_9$-aralkyl, or (5) the group —($C_pH_{2p}$)—CO—$OR_{15}$, in which $R_{15}$ is $C_1$-$C_{18}$-alkyl, and p denotes 1 to 6, and $R_{12}$ and $R_{13}$ independently represent (1) hydrogen, (2) $C_1$-$C_{18}$-alkyl, (3) $C_3$-$C_4$-alkenyl, (4) $C_5$-$C_7$-cycloalkyl, (5) $C_6$-$C_{10}$-aryl, (6) $C_7$-$C_9$-aralkyl or (7) a radical of the formula II as defined above, and $R_{14}$ denotes $C_1$-$C_{18}$-alkyl, $C_6$-$C_{10}$-aryl or $C_7$-$C_9$-aralkyl; and B is (1) a radical of the formula IV or V as defined above or (2) —P(=O)(OR$_1$)OR$_2$, in which $R_1$ is a radical of the formula II or III as defined above and $R_2$ is as defined above.

2. A compound according to claim 1, wherein $R_1$ is (1) $C_1$-$C_{12}$-alkyl, (2) naphthyl, (3) phenyl, (4) $C_7$-$C_9$-aralkyl or (5) a radical of the formula II or III; $R_2$ is (1) $C_1$-$C_{12}$-alkyl, (2) naphthyl, (3) phenyl or (4) $C_7$-$C_9$-aralkyl, $R_3$ is hydrogen or $C_1$-$C_4$-alkyl and $R_4$ is (1) hydrogen, (2) oxyl, (3) $C_1$-$C_8$-alkyl, (4) $C_3$-$C_4$-alkenyl, (5) $C_3$-$C_4$-alkinyl, (6) $C_2$-$C_6$-alkoxy-alkyl, (7) $C_7$-$C_9$-aralkyl, (8) acetyl, (9) acryloyl, (10) crotonoyl, (11) —CH$_2$—COOR$_5$, (12) —CH$_2$—CH(R$_6$)—OR$_7$, (13) —COOR$_8$ or (14) —CONHR$_8$, wherein $R_5$ is (1) $C_1$-$C_4$-alkyl, (2) $C_3$-$C_4$-alkenyl, (3) phenyl, (4) $C_7$-$C_8$-aralkyl, or (5) cyclohexyl, $R_6$ is hydrogen, methyl or phenyl, $R_7$ denotes (1) hydrogen or (2) an aliphatic-, aromatic-, alicyclic- or araliphatic-acyl group having 1–18 C atoms, wherein the aromatic portion is unsubstituted or substituted by at least one member of the group or chlorine, $C_1$-$C_4$-alkyl or $C_1$-$C_8$-alkoxy and hydroxyl, and $R_8$ is $C_1$-$C_{12}$-alkyl; A is (1) a radical of the formula IV or V, wherein $R_3$ and $R_4$ are as defined in claim 1, n is 2, $R_9$ is hydrogen or hydroxyl, Y is —O— or —$NR_{10}$—, wherein $R_{10}$ is (a) hydrogen, (b) straight-chain $C_1$-$C_8$-alkyl or (c) a radical of the formula II, or (2) A is —P(=O)(OR$_1$)OR$_2$, —S—$R_{11}$, —$NR_{12}R_{13}$ or —$OR_{14}$, in which $R_1$ and $R_2$ are as defined in claim 1, $R_{11}$ represents $C_1$-$C_8$-alkyl or the group —($C_pH_{2p}$)—CO—$OR_{15}$, in which $R_{15}$ represents $C_1$-$C_{18}$-alkyl and p is 1 to 4, and $R_{14}$ is $C_1$-$C_{12}$-alkyl and $R_{12}$ and $R_{13}$ independently represent (1) hydrogen, (2) $C_1$-$C_{12}$-alkyl, (3) phenyl or (4) a radical of the formula II; and B is (1) a radical of the formula IV or V, or (2) is —P(=O)(OR$_1$)OR$_2$ in which $R_1$ is a radical of the formula II or III, and $R_2$ is as defined in claim 1.

3. A compound according to claim 1, wherein $R_1$ is $C_1$-$C_3$-alkyl or a radical of the formula II; $R_2$ is $C_1$-$C_3$-alkyl, $R_3$ represents hydrogen, methyl or ethyl and $R_4$ is (1) hydrogen, (2) $C_1$-$C_4$-alkyl, (3) allyl, (4) propargyl, (5) $C_2$-$C_6$-alkoxyalkyl, (6) acetyl, (7) acryloyl, (8) crotonoyl, (9) —CH$_2$—COOR$_5$, (10) —CH$_2$—CH(R$_6$)—OR$_7$, (11) —COOR$_8$ or (12) —CONHR$_8$, wherein $R_5$ is $C_1$-$C_4$-alkyl and $R_6$ represents hydrogen or methyl, $R_7$ represents hydrogen and $R_8$ is $C_1$-$C_4$-alkyl; A is (1) a radical of the formula IV or V, in which $R_3$ and $R_4$ are as defined in claim 1 and n is 2 and $R_9$ is hydrogen or hydroxyl, Y is —$NR_{10}$—, in which $R_{10}$ is hydrogen or a radical of the formula II, or (2) A is —P(=O)(OR$_1$)OR$_2$, in which $R_1$ and $R_2$ are as defined in claim 1; and B is (1) a radical of the formula IV or V, in which $R_3$ and $R_4$ are as defined in claim 1, n is 2 and $R_9$ is hydrogen or hydroxyl, or (2) B is —P(=O)(OR$_1$)OR$_2$, in which $R_1$ is a radical of the formula II and $R_2$ is as defined in claim 1.

4. A compound according to claim 1, wherein $R_1$ is $C_1$-$C_3$-alkyl or a radical of the formula II; $R_2$ is $C_1$-$C_3$-alkyl, $R_3$ represents hydrogen or methyl and $R_4$ denotes hydrogen or methyl; A is (1) a radical of the formula IV or V, in which $R_3$ and $R_4$ are as defined in claim 1, n is 2 and $R_9$ is hydrogen or hydroxyl, Y is —$NR_{10}$—, in which $R_{10}$ is hydrogen or a radical of the formula II, or (2) A is —P(=O)(OR$_1$)OR$_2$, in which $R_1$ and $R_2$ are as defined in claim 1; and B is (1) a radical of the formula IV or V, in which $R_3$, $R_4$ and n are as defined in claim 1, and $R_9$ is hydrogen or hydroxyl, or (2) B is —P(=O)(OR$_1$)OR$_2$, in which $R_1$ is a radical of the formula II and $R_2$ is as defined in claim 1.

5. A compound according to claim 1, said compound being 2-(diethylphosphono)-4,6-bis-[2,2,6,6-tetramethyl-piperidin-4-yl)-amino]-1,3,5-triazine.

* * * * *